United States Patent
Haas et al.

[11] Patent Number: 6,007,649
[45] Date of Patent: Dec. 28, 1999

[54] METHOD OF PRODUCING PRESS-MOULDING MATERIALS WITH POLYISOCYANATE BINDERS AND USING LATENT, HEAT-ACTIVABLE CATALYSTS

[75] Inventors: Peter Haas, Haan; Peter Vehlewald, Leichlingen; Peter Kasperek, Much, all of Germany

[73] Assignee: Bayer Aktiengesellschaft, Leverkusen, Germany

[21] Appl. No.: 09/117,100

[22] PCT Filed: Jan. 20, 1997

[86] PCT No.: PCT/EP97/00237

§ 371 Date: Jul. 22, 1998

§ 102(e) Date: Jul. 22, 1998

[87] PCT Pub. No.: WO97/28202

PCT Pub. Date: Aug. 7, 1997

[30] Foreign Application Priority Data

Jan. 31, 1996 [DE] Germany ............... 196 03 330

[51] Int. Cl.$^6$ ................................. C08G 18/18
[52] U.S. Cl. ............... 156/62.2; 156/296; 156/333.4; 264/109
[58] Field of Search ................... 156/62.2, 296, 156/333.4; 264/109

[56] References Cited

U.S. PATENT DOCUMENTS

| | | |
|---|---|---|
| 4,186,255 | 1/1980 | Klein et al. . |
| 4,331,778 | 5/1982 | Sommerfeld et al . |
| 4,376,089 | 3/1983 | Bogner et al. . |
| 4,490,517 | 12/1984 | Fuzesi et al. . |
| 4,546,165 | 10/1985 | Grogler et al. . |
| 4,608,407 | 8/1986 | Kerimis et al. . |
| 4,632,785 | 12/1986 | Barsa . |
| 4,935,457 | 6/1990 | Metzner et al. . |

FOREIGN PATENT DOCUMENTS

| | | |
|---|---|---|
| 2122368 | 3/1994 | Canada . |
| 2711958 | 8/1981 | Germany . |

*Primary Examiner*—Sam Chuan Yao
*Attorney, Agent, or Firm*—Joseph C. Gil; Lyndanne M. Whalen

[57] ABSTRACT

A process is described for producing pressed materials, particularly wood particle boards, by the hot compaction of raw materials containing lignocellulose which are mixed and/or impregnated with polyisocyanates as binders, with the use of latent, thermally activatable catalysts, wherein ammonium salts from the reaction of amines with malonic acid are used as catalysts.

8 Claims, No Drawings

METHOD OF PRODUCING PRESS-MOULDING MATERIALS WITH POLYISOCYANATE BINDERS AND USING LATENT, HEAT-ACTIVABLE CATALYSTS

A process is claimed for producing pressed materials, preferably particle boards, by the hot compaction of raw materials containing lignocellulose which are mixed and/or impregnated with polyisocyanates as binders, with the use in conjunction of new types of latent, thermally activatable catalysts based on ammonium salts, such as those produced by the reaction of primary, secondary and/or tertiary amines with malonic acid.

Pressed materials, such as particle boards, composite boards or other moulded bodies for example, are usually produced by the hot compaction, as a so-called mixed bonding system, of an inorganic or organic raw material, e.g. a composition comprising wood chips, wood fibres and/or other material containing lignocellulose, with polyisocyanates and water, optionally with polyols or other binders such as urea/formaldehyde or phenol/formaldehyde resins. The use of polyisocyanates as binders improves the stability of the products and their behaviour under humid conditions, and enhances their mechanical properties. In addition, polyisocyanates as binders possess extensive process technology advantages, as disclosed in DE-OS 2 109 686 for example.

In principle, catalysts of the type which are known in the art from polyurethane chemistry, e.g. those which are cited in DE-OS 2 854 384 on pages 26 to 29 and 31 to 33, can also be used in conjunction in prior art processes (see DE-AS 2 711 958 for example) to reduce the pressing times. This is particularly important in what are termed single daylight presses. However, this usage generally results in unwanted foam formation and premature bonding, even during the mixing of the components and the storage of the wood chips bonded with isocyanates before compaction; this is due to the action of the catalyst on the reactive NCO groups, which occurs immediately. For this reason, the conjoint use of catalysts mostly has to be avoided and longer pressing times have to be accepted.

A process is known from EP 133 680 for producing pressed materials using urethanes as binders, in which tertiary or quaternary ammonium phosphonates or quaternary ammonium phosphates are used as thermally activatable catalysts. Even when these catalysts are used, the reduction in pressing time which is observed is always not always quite sufficient for the process to be carried out economically. Moreover, pressing times which are sufficiently short cannot be achieved using the processes described in DE 4 229 396 and DE 3 438 735 for producing particle boards or fibre boards using polyisocyanates as binders.

The object of the present invention is therefore to provide a latent catalyst system for the production of pressed materials containing polyisocyanate binders, which is capable of activating the reactions of polyisocyanates at elevated temperatures but which does not exhibit catalytic behaviour at temperatures up to 80° C.

This catalyst system can even be admixed with the polyisocyanate used, or with the formulation which is used for the production of pressed bodies and which comprises polyisocyanates, water, materials containing lignocellulose such as fibres, wood chips or straw-like fibres, and other polyhydroxyl compounds which are optionally to be used in conjunction, without unwanted reactions occurring at room temperature and on mixing and storage at temperatures up to 80° C. However, the pressing times can be considerably reduced due to the more rapid bonding during pressing which takes place as a result of the catalysis which becomes effective at higher temperatures. Surprisingly, it has now been found that the catalysts described in detail below, which are based on amine salts of malonic acid, are very suitable for the object described, since up to 80° C. they constitute latent catalysts in the polyisocyanate formulation but at pressing temperatures they catalyse isocyanate reactions and thus fulfil the conditions specified above.

The present invention relates to a process for producing pressed materials, preferably wood particle boards, by the hot compaction of raw materials containing lignocellulose which are mixed and/or impregnated with polyisocyanates as binders, with the use of thermally activatable catalysts, characterised in that ammonium salts from the reaction of amines with malonic acid are used as catalysts.

The ammonium salts to be used according to the invention are preferably those which can be obtained by the reaction of mono- or polyfunctional, primary, secondary or tertiary amines with malonic acid.

In this respect, all amines, such as those which are cited in EP 133 680 for example, can be used as the amine component of the ammonium salts to be used according to the invention. Tertiary amines are particularly preferred, especially N,N-dimethylaminoethanol, dimethylaminopropylurea, bis-2,2'-dimethylaminoethylether, N-methylimidazole and N-methyl-2-azanorboinane.

The ammonium salts to be used according to the invention can be obtained by the reaction of the amines cited by way of example with malonic acid.

The preparation of ammonium salts of malonic acid is known in principle to one skilled in the art. For this purpose the amines are usually dissolved in water and subsequently neutralised with malonic acid, wherein equimolar amounts of amine and malonic acid are preferably used.

The surprising nature of the latency effect at 60–80° C. and of the activation effect above 100° C. is accentuated even more in that malonic acid intrinsically constitutes the most thermally labile of the dicarboxylic acid series, and therefore the opposite behaviour as regards the latency phase would be expected in principle.

This applies not only to the ammonium salts of malonic acid which are neutralised with stoichiometric equivalence, but is also applicable to products which are neutralised incompletely and which are accordingly present in acidic, i.e. partially neutralised, form.

The reaction of malonic acid to form the ammonium malonates according to the invention can be effected in water or can be effected just as advantageously in solvents which are inert to isocyanates, such as dimethylacetamide, N-methylpyrrolidone, N-methylcaprolactam or N,N'-dimethylimidazolidone for example. These solvents enable the isocyanates which are sprayed on to the wood materials to be doped with the latent activators.

The aqueous solutions are processed upstream.

The catalysts to be used according to the invention are generally colourless solutions in water or organic solvents which contain ammonium salts of malonic acid. At temperatures below 80° C. the catalysts according to the invention are without appreciable catalytic activity in relation to the isocyanate addition reaction. The catalysts used according to the invention first exhibit a pronounced catalytic effect at temperatures above 90° C., particularly within the temperature range of 90–150° C., preferably 90–110° C. It is thereby ensured on the one hand that the storage stability of the reaction mixtures of polyisocyanates and raw materials which contain the catalysts according to the invention is only slightly less than the storage stability of corresponding uncatalysed reaction mixtures at the temperatures cited, whilst on the other hand the desired, pronounced speeding up of the isocyanate addition reaction occurs at higher temperatures within the cited ranges. This thus results, in an advantageous manner, in a shortening of the pressing time.

The catalysts according to the invention may also of course be dissolved in modified polyisocyanate binders, e.g.

in aqueous polyisocyanate emulsions such as those obtained by the addition of emulsifiers such as polyethylene glycols, bonding agent, polyvinyl pyrrolidone or polyacrylamides, which optionally also contain polyethylene dispersions and wood preservatives, or in modified aqueous polyisocyanate emulsions which are made hydrophilic by modification with monofunctional polyethylene oxide derivatives or by the addition of phosphoric or sulphonic acids.

Aliphatic, cycloaliphatic, araliphatic, aromatic and heterocyclic polyisocyanates are suitable as the isocyanate component for carrying out the process according to the invention, such as those which are described, for example, by W. Siefken in Justus Liebigs Annalen der Chemie 562, pages 75 to 136, for example those of formula

where n is 2 to 4, preferably 2, and

Q represents an aliphatic hydrocarbon radical containing 2 to 18, preferably 6 to 10 carbon atoms, a cycloaliphatic hydrocarbon radical containing 4 to 23, preferably 5 to 13 C atoms, an aromatic hydrocarbon radical containing 6 to 23, preferably 6 to 13 C atoms, or an araliphatic hydrocarbon radical containing 8 to 15, preferably 8 to 13 C atoms, e.g. 4,4'-diphenylmethane diisocyanate, 1,3- and 1,4-phenylene diisocyanate, toluene 2,4- and 2,6-diisocyanate and any mixtures of these isomers, diphenylmethane 2,4'- or 4,4'-diisocyanate and any mixtures of these isomers, or the polymeric types of this series.

Polyisocyanates which are readily accessible industrially are generally preferred, e.g. toluene 2,4- and 2,6-diisocyanate and any mixtures of these isomers ("TDI"), and also, most preferably, polyphenyl-polymethylene polyisocyanates such as those which are produced by aniline-formaldehyde condensation and subsequent phosgenation ("crude MDI"). The polyisocyanates used may also optionally be modified. Isocyanates with nuclei of higher mass, of the phenylmethane diisocyanate series (PMDI types), are most preferably used as the polyisocyanate component.

Prepolymers which contain terminal isocyanate groups and which have an average molecular weight of about 300 to 2000 can also be used for carrying out the process according to the invention, such as those which are obtained in the manner known in the art by the reaction of higher molecular weight and/or low molecular weight polyols with an excess of polyisocyanate.

All the higher molecular weight polyols which are commonly used in polyurethane chemistry can be used as polyols, particularly compounds containing two to eight hydroxyl groups, especially those with molecular weights of 400 to 10,000, preferably 600 to 5000, e.g. polyesters, polyethers, polythioethers, polyacetals, polycarbonates and polyester amides containing at least two, generally two to eight, but preferably two to four hydroxyl groups, such as those which are known in the art, for example, for the production of homogeneous and cellular polyurethanes.

Examples of suitable raw materials which contain lignocellulose and which can be bonded with the polyisocyanate-activator formulation according to the invention, include wood, bark, cork, bagasse, straw, flax, bamboo, alfa grass, rice husks, and sisal and coconut fibres. The material may be present in the form of granules, chips, fibres or flour, and may have a water content, for example, of 0 to 35% by weight, preferably from 5 to 25% by weight. It is mixed with the binder in an amount of 1 to 100, preferably 2 to 12% by weight and is compacted—generally under the effect of pressure and heat—to form boards or moulded bodies.

0.1 to 20, preferably 0.1 to 15% by weight of the catalyst according to the invention is used with respect to the polyisocyanate binder.

However, pressed bodies can also of course be produced according to the invention from other organic raw materials (e.g. plastics of all types) and/or inorganic raw materials (e.g. expanded mica or silicate spheres).

In the use according to the invention, the material to be compacted is mixed with the binder, advantageously by spraying with the binder according to the invention, in order to obtain a distribution which is as homogeneous as possible.

In practice, periods of delay may occur between the individual process steps (preparation of the formulation: spraying the material to be used), and delays may occur as a result of operating errors or as a result of resetting the process conditions. However, it is desirable that the speeding up of the isocyanate reactions of the correspondingly bonded wood materials by the catalysts according to the invention proceeds sufficiently slowly at temperatures up to 80° C. so that a delay from at least 2 hours up to several hours can be accepted, particularly at low temperatures, between the preparation of the isocyanate-activator formulation and hot compaction. The reaction rate can be reduced even further by modifying the reactivity of the polyisocyanates. Thus, for example, the reaction rate can be significantly reduced by an increased proportion of 2,4'- and/or 2,2'-diphenylmethane diisocyanate (in relation to the 4,4'-isomer).

In an analogous manner, multi-layer boards or mouldings can also be produced from veneers, paper or fabrics. Multi-layer boards or mouldings comprising veneers and middle layers of strips, slats or small sticks, which are termed table boards, can also be produced according to the invention by treating the veneers with the isocyanate-activator formulation as described above and subsequently compacting it with the middle layers—generally at elevated temperature and under pressure. Temperatures of 80 to 250° C., most preferably 100 to 220° C., are maintained in this respect. The initial compaction pressure is also preferably between 5 and 150 bar here; the pressure then generally falls to zero in the course of the pressing operation.

According to the invention, the polyisocyanate-activator formulations may also be used in combination with the polyhydroxyl compounds described above at an NCO/OH ratio of 1.1:1 to 10:1, preferably 1.5:1 to 5:1. In this respect, it is possible to use the two components separately or as a reactive mixture. Combinations of polyisocyanate and polyhydroxyl compounds of this type are of practical importance as binders, in the bonding of cork scrap for example. It is also possible to add foaming agents known in the art in an amount of about 0.5 to 30% by weight with respect to the binder or impregnating agent, and/or to add other additives such as stabilisers, which influence foam formation or the chemical reaction between polyisocyanates and the material containing lignocellulose and optionally polyhydroxyl compounds, in an amount of 0.05 to 10% by weight with respect to the binder or impregnating agent.

The polyisocyanate-activator formulations which are to be used as binders according to the invention may also be combined with the aqueous solutions of condensation products of formaldehyde and urea and/or melamine and/or phenol (mixed bonding systems) which have hitherto predominantly been used in the timber materials industry, but may also be combined with other binders and impregnating agents which were less customary hitherto, such as sulphite liquor (lignin sulphonate or other industrial solutions of lignin from the digestion of wood), or tanniferous compounds such as tannin, for example, where a mixture ratio of the binders according to the invention to these additional binders between 1:10 and 10:1, preferably between 1:5 and 5:1, can be maintained for example, and wherein the binders according to the invention and the additional binders can be used either separately or in admixture.

Combinations of this type are particularly advantageous in the production of multi-layer boards with special properties. For example, the outer layers may be treated with conventional adhesives (on their own or together with the polyisocyanate binder) and one or more inner layers may be treated with the polyisocyanate binder to be used according to the invention (on its own or together with conventional adhesives) and subsequently compacted with each other.

In the production of particle boards, particularly multi-layer particle boards, the problem often arises of completely reacting the chips with the polyisocyanate binders, even in the middle layers of the particle boards, using pressing times which are as short as possible. The advantage of the latently active, thermally activatable catalysts according to the invention has a particularly favourable effect here, because the catalyst is used directly in the middle layers and accelerated bonding thus occurs here, even though the heating of the middle layer inevitably occurs from the outside, with a relative delay. The high temperature which acts from the pressing tool firstly heats up the outer layers strongly and results in a steam shock which transmits the temperature Oust above 100° C.) into the interior of the particle boards. Even at this temperature, the catalyst-containing polyisocyanate binders in the middle layer then react within a considerably shortened period of time. Further significant shortening of this timescale can scarcely be achieved, since heat transfer into the middle layer cannot occur more rapidly. Accordingly, it is preferable only to activate the middle layer according to the invention and to formulate the outer layers without a catalyst. However, bonding of the chips of the outer layer may also be effected using polyisocyanates containing an activator, but this results in no significant change, since the effect which is essential to success is satisfactory bonding in the middle layer. In practice, the satisfactory bonding of the chips in the layers is monitored by measuring the thickness or increase in thickness of the boards formed after they leave the press.

As a result of their outstanding mechanical properties, the boards or mouldings produced according to the invention, which are based on organic raw materials containing lignocellulose or other organic and/or inorganic raw materials, are primarily suitable for use in the building trade. In order to provide the boards or mouldings with the resistance to fungal attack, attack by insects or the effects of fire which are generally necessary for this purpose, commercially available additives, e.g. aqueous polyethylene emulsions or organic or inorganic preservatives, may be added in pure form or as a solution to the binders or the raw materials, in an amount of about 0.05 to 30% by weight, preferably 0.5 to 20% by weight, with respect to the material as a whole. Suitable solvents include: water or organic solvents, e.g. residual oils from the processing of crude oil, chlorinated hydrocarbons, etc. The quality of the bonding is not generally impaired thereby. In contrast to boards bonded with phenol/formaldehyde resin, it is advantageous that neither salt bloom nor "bleeding" occurs with the materials produced according to the invention.

Due to the high adhesive power of the binders according to the invention, mouldings which are impregnated or bonded with them frequently tend to adhere to the surfaces of hot presses or moulds. This can be prevented by release agents which are added to the binders. Another solution consists of applying release agents in pure form or as a solution to metallic surfaces which come into contact with the pressed articles or to the surface of the moulding. All the substances which have hitherto been proposed for this purpose are suitable as external release agents. However, compounds according to DE-OS 2 325 926 which catalyse the formation of urethane with isocyanates are preferred, for example phenol-Mannich bases, derivatives of hexahydrotriazine or alkali salts of carboxylic acids and/or soaps, optionally in solution, such as aqueous diethylene glycol for example. Another solution to the problem of eliminating adhesion consists of providing a parting layer between the article to be pressed and the metallic surface of the press, wherein the parting layer may consist of lengths, sheets or broken material comprising different raw materials (e.g. plastics, paper, wood, metal). As has been repeatedly mentioned above, significant improvements in the production of particle boards, both as regards mechanical properties and from a process technology point of view, can be achieved with the isocyanate binders to be used according to the invention compared with conventional binders based on phenol/formaldehyde or urea/formaldehyde resins. Thus in the case of wood particle boards it is possible either to obtain a bending strength which is increased by up to 50% (in addition to an improvement in other mechanical properties) using the same amount of binder as for phenol/formaldehyde or urea/formaldehyde resins, or to obtain the same range of mechanical properties at a binder concentration which is reduced by about 25 to 70%.

The following examples explain the invention. Numerical data are to be understood as parts by weight or percentage by weight unless otherwise indicated.

EXAMPLES

Experimental Part

A) Latent Activators

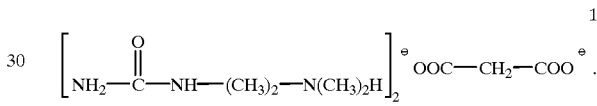

From 290 g (2.0 moles) 3-N,N-dimethylaminopropylurea and 131.3 g water, reacted at 15° C. with 104.1 g (1.0 mole) malonic acid. Acid number: 210 Amine number: 210

2. Partially neutralised form of 1.

From 253.7 g (1.75 moles) N,N-dimethylaminopropylurea and 119.2 g water, reacted at 15° C. with 104.1 g (1.0 mole) malonic acid. Acid number: 235 Amine number: 205

3. Partially neutralised form of 1.

From 217.5 g (1.50 moles) N,N-dimethylaminopropylurea and 107.1 g water, reacted at 15° C. with 104.1 g (1.0 mole) malonic acid. Acid number: 261 Amine number: 196

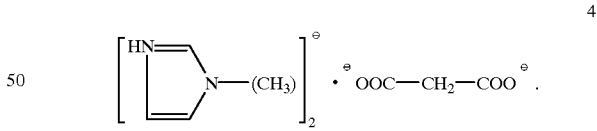

From 164.2 g (2.0 moles) N-methylimidazole and 89.3 g water, reacted at 15° C. with 104.1 g (1.0 mole) malonic acid. Acid number: 313 Amine number: 313

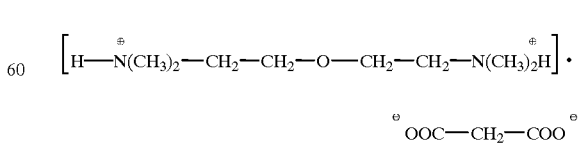

From 160 g (1.0 moles) bis-(2-N,N-dimethylaminoethyl) ether and 88.0 g water, reacted at 15° C. with 104.1 g (1.0 mole) malonic acid. Acid number: 315 Amine number: 314

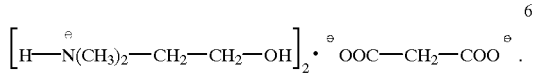

From 178 g (2.0 moles) 2-N,N-dimethylaminoethanol and 94 g water, reacted at 15° C. with 104.1 g (1.0 mole) malonic acid. Acid number: 296 Amine number: 295

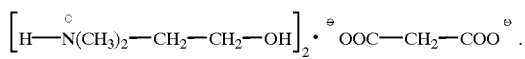

From 178 g (2.0 moles) 2-N,N-dimethylaminoethanol and 94 g N,N-dimethylacetamide, reacted at 15° C. with 104.1 g (1.0 mole) malonic acid. Acid number: 295 Amine number: 293

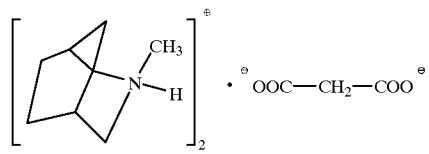

From 222 g (2.0 moles) N-methyl-2-azanorbornane and 108 g water, reacted at 15° C. with 104.1 g (1.0 mole) malonic acid. Acid number: 258 Amine number: 251

9. (Comparative)

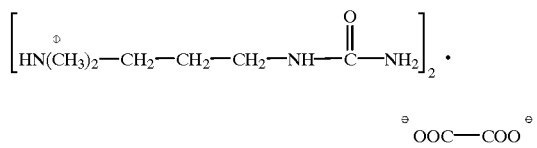

From 290 g (2.0 moles) 3-N,N-dimethylaminopropylurea and 380.0 g water, reacted at 15° C. with 90.1 g (1.0 mole) oxalic acid. Acid number: 146 Amine number: 145

10. (Comparative)

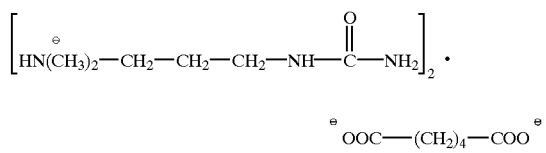

From 290 g (2.0 moles) 3-N,N-dimethylaminopropylurea and 145.3 g water, reacted with 146 g (1.0 mole) adipic acid at 15° C. Acid number: 191 Amine number: 190

Example of Application to the Production of a Three-Layer Board

A) Middle Layer 2250 parts by weight of middle layer chips, which consisted of a mixture of coniferous wood and deciduous wood and had a moisture content of about 10%, were bonded with 102 parts by weight of Desmodur VPPU 1520A20L polyisocyanate supplied by Bayer AG. The amount of the catalysts according to the invention which were used is given in Tables 1 and 2.

B) Upper and Lower Layer 980 parts by weight of chips with a moisture content of 15% were bonded with 43 parts by weight of Desmodur VPPU 1520A20L polyisocyanate supplied by Bayer AG. A 3-layer formed body was produced, of size 580×520 mm and with an upper and lower layer of 10 mm and a middle layer of 20 mm; this was compacted at 180° C. The metal press plattens were previously treated with the release agent Baysilon LAV supplied by Bayer AG. The V 100 transverse strength of the particle boards obtained (thickness 16 mm) was determined according to DIN 68 763 after various pressing times.

TABLE 1

| Catalyst solution in the middle layer | Pressing time at 180° C. 1.6 minutes |
|---|---|
| without catalyst | 0.09 MPa |
| 10% catalyst | 0.16 MPa |
| 5% catalyst | 0.15 MPa |
| 1% catalyst | 0.15 MPa |

TABLE 2

| Catalyst solution | Pressing time at 180° C. | |
|---|---|---|
| in the middle layer | 1.85 minutes | 1.45 minutes |
| without catalyst | 0.17 | * |
| 5% catalyst according to Example 6 | 0.21 | 0.18 MPa |
| 1% catalyst according to Example 6 | 0.16 | 0.15 MPa |

*not measurable; fragile

TABLE 3

| Ammonium salt of | Latency effect at 60 to 80° C. | continuous bonding reaction at 100° C. |
|---|---|---|
| oxalic acid (according to Example 9; comparative) | good | poor |
| malonic acid (according to Example 1) | good | good |
| adipic acid (according to Example 10; comparative) | poor | poor |
| maleic acid (comparative) | poor | poor |
| methylphosphonic acid (comparative) according to EP 133 680 | unsatisfactory | unsatisfactory |

Results:

Comparative tests with the addition of amines blocked with oxalic acid, adipic acid and maleic acid were also performed in an analogous manner, as listed in Table 3. For comparison with the prior art, a test was also performed using a thermally activatable catalyst based on ammonium salts of phosphonic acid according to EP 133 680.

Compared with the ammonium salts of other acids listed in table 3, the outstanding sample containing ammonium salts of malonic acid was distinguished by its latency phase up to 80° C. which is required for the production of particle boards and by its catalysis of the continuous bonding reaction at a middle layer temperature of 100 to 110° C.

We claim:

1. A process for producing pressed articles from a lignocellulose-containing material comprising:
    a) applying a polyisocyanate binder containing an ammonium salt of malonic acid catalyst that is a reaction product of malonic acid and a compound selected from the group consisting of N,N-dimethylaminoethanol, dimethylaminopropyl urea, bis-(2-N,N-dimethylaminoethyl) ether, N-methylimidazole, N-methyl-2-azanorbornane, and combinations thereof to the lignocellulose-containing material and
    b) heating the product of a) under pressure to form the desired pressed article.

2. The process of claim 1 in which the ammonium salt of malonic acid used as the binder catalyst is the reaction product of a tertiary amine and malonic acid.

3. The process of claim 1 in which the ammonium salt of malonic acid used as the binder catalyst is present in the binder in an amount of from 0.1 to about 20% by weight, based on the weight of the polyisocyanate binder.

4. The process of claim 1 in which the ammonium salt of malonic acid used as the binder catalyst is present in the binder in an amount of from 0.1 to about 15% by weight, based on the weight of the polyisocyanate binder.

5. The process of claim 1 in which a binder based on urea/formaldehyde, melamine/formaldehyde, phenol/formaldehyde or a combination thereof is also applied to the lignocellulose-containing material.

6. The process of claim 1 in which a release agent, wood preservative, flame retardant, polyethylene dispersion or a combination thereof is also applied to the lignocellulose-containing material.

7. The process of claim 1 in which polymeric methylene diisocyanate is the polyisocyanate in the polyisocyanate binder.

8. The process of claim 1 in which polymeric methylene diisocyanate which has been modified with a polyether polyol or a polyester polyol is the polyisocyanate in the polyisocyanate binder.

\* \* \* \* \*